Figure 1:
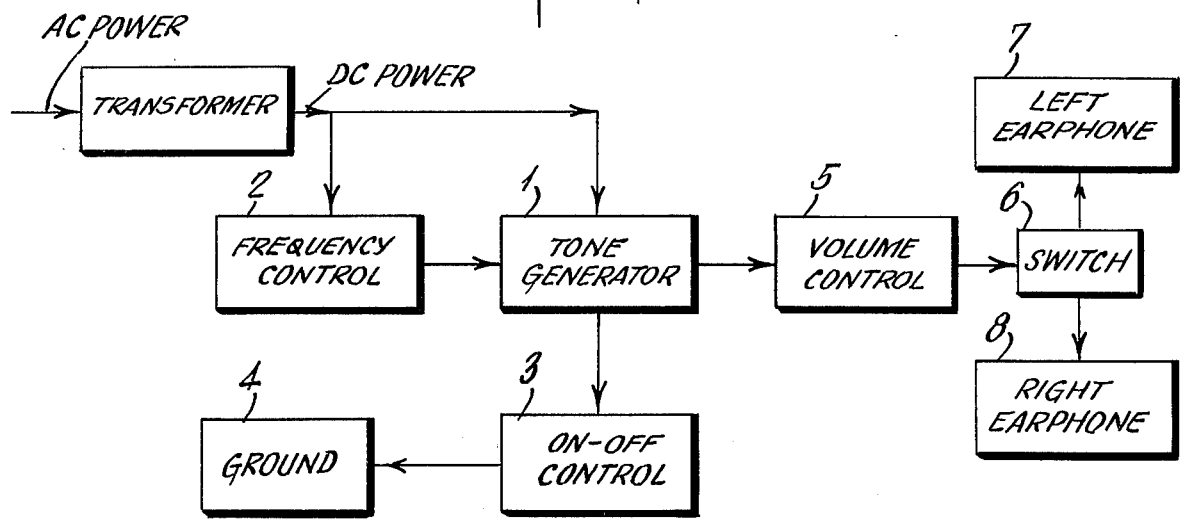

United States Patent [19]

Krass

[11] 4,022,975

[45] May 10, 1977

[54] PSYCHOLOGICAL TESTING APPARATUS

[75] Inventor: Alvin Krass, Holmdel, N.J.

[73] Assignee: Alvin Krass, Holmdel, N.J.

[22] Filed: Mar. 15, 1976

[21] Appl. No.: 666,781

[52] U.S. Cl. ............................................. 179/1 N
[51] Int. Cl.² .......................................... A61B 5/12
[58] Field of Search ................................. 179/1 N

[56] References Cited
UNITED STATES PATENTS

| 3,718,763 | 2/1973 | Cannon et al. | 179/1 N |
| 3,793,485 | 2/1974 | Feezor et al. | 179/1 N |
| 3,809,811 | 5/1974 | Delisle et al. | 179/1 N |

Primary Examiner—Kathleen H. Claffy
Assistant Examiner—E. S. Kemeny
Attorney, Agent, or Firm—Harry E. Westlake, Jr.

[57] ABSTRACT

An apparatus is described which, in addition to testing each ear of a human subject separately for extent of hearing and frequency detection, also permits the delivery, preferably by electronic means for pre-set arrangement, of a series of intermittent long and short signals in different combinations, by means of which the subject can be tested for auditory memory and hearing side dominance.

6 Claims, 4 Drawing Figures

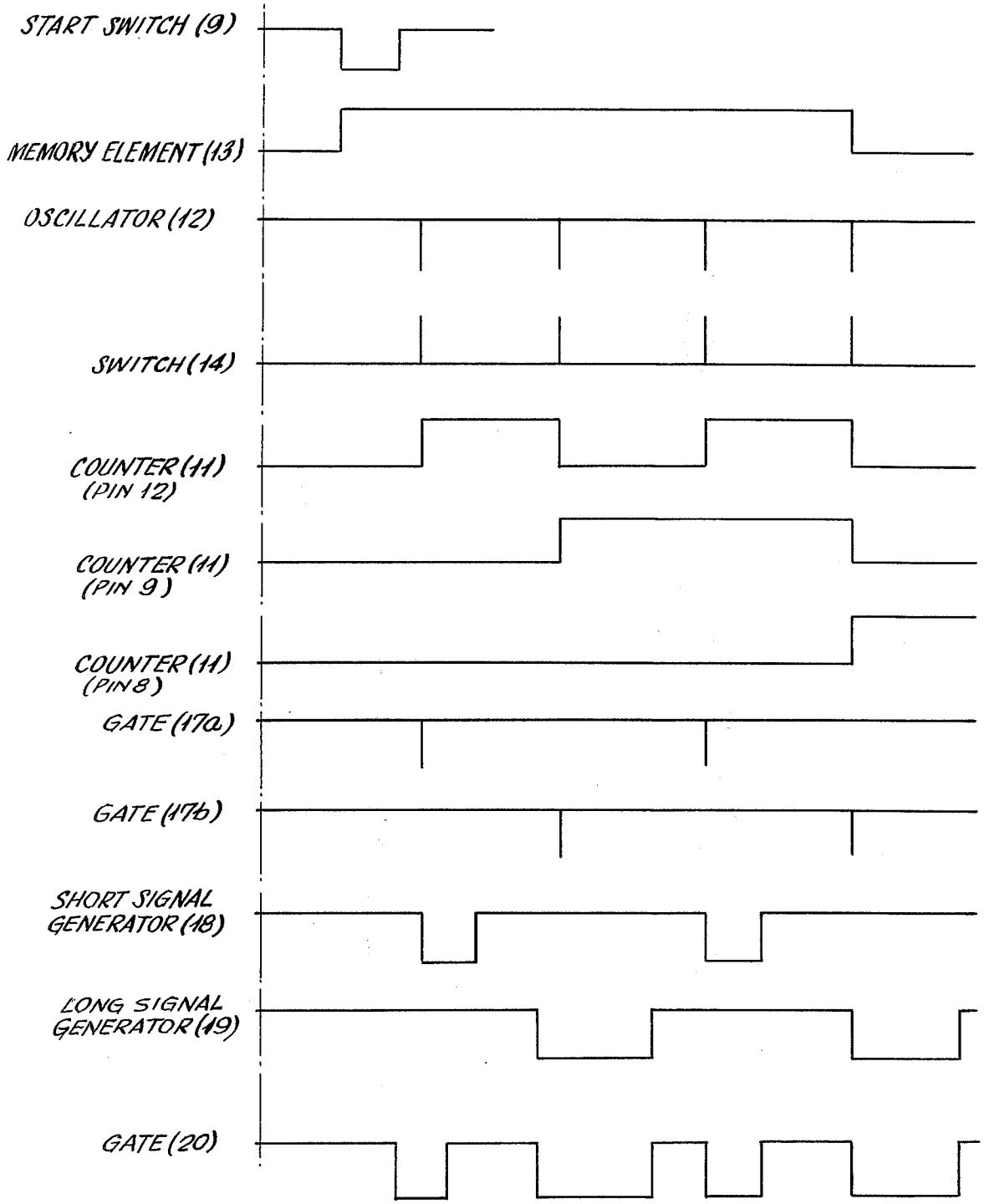

PSYCHOLOGICAL TESTING APPARATUS

This invention relates to a compact portable educational and psychological testing apparatus for measuring hearing, auditory memory and hearing side dominance. More specifically, it relates to such an apparatus which comprises, in combination, an electronic means for generating audible frequencies, means for converting said frequencies into sounds delivered separately to individual human ears, means for controlling the delivery of sounds into one or the other or both ears, means for delivering said sounds continuously or as interrupted pulses, means for controlling the audible volume and means for controlling the tone or frequency of said sounds.

BACKGROUND OF THE INVENTION

In the past there have been available machines which, individually, performed certain functions needed in educational and/or psychological testing. There have been many devices to measure the minimum loudness which a human ear could detect and they have permitted the testing of the ears individually or together. There have been other devices which attempted to measure the auditory memory of humans being tested. These prior instruments have been separate from one another and each a complicated and expensive machine. Each test for loudness capable of being heard, of auditory memory, or auditory side-dominance, etc. needed a separate, expensive apparatus. In some cases the apparatus has been unreliable or at best required careful calibration.

THE INVENTION

The present invention has many advantages over the previously available instruments. It is simple, compact and portable. It accomplishes in one small instrument what previously took a whole group of prior complex instruments to measure.

This invention has as its purpose the screening of humans rapidly and efficiently for a number of attributes, by means of a portable compact instrument which can be taken anywhere for convenient use. One such attribute to be tested is the sensitivity of each ear individually to varying volumes and frequencies, to determine whether any deafness is involved. Secondly, it is intended to determine whether one ear is more functional than the other in the hearing process, especially whether other mental functions depending on the auditory sense are dependent more on one ear than the other. Thirdly, it has the capacity to test the auditory memory of the subject and its relation to the individual ears.

Figure 2:
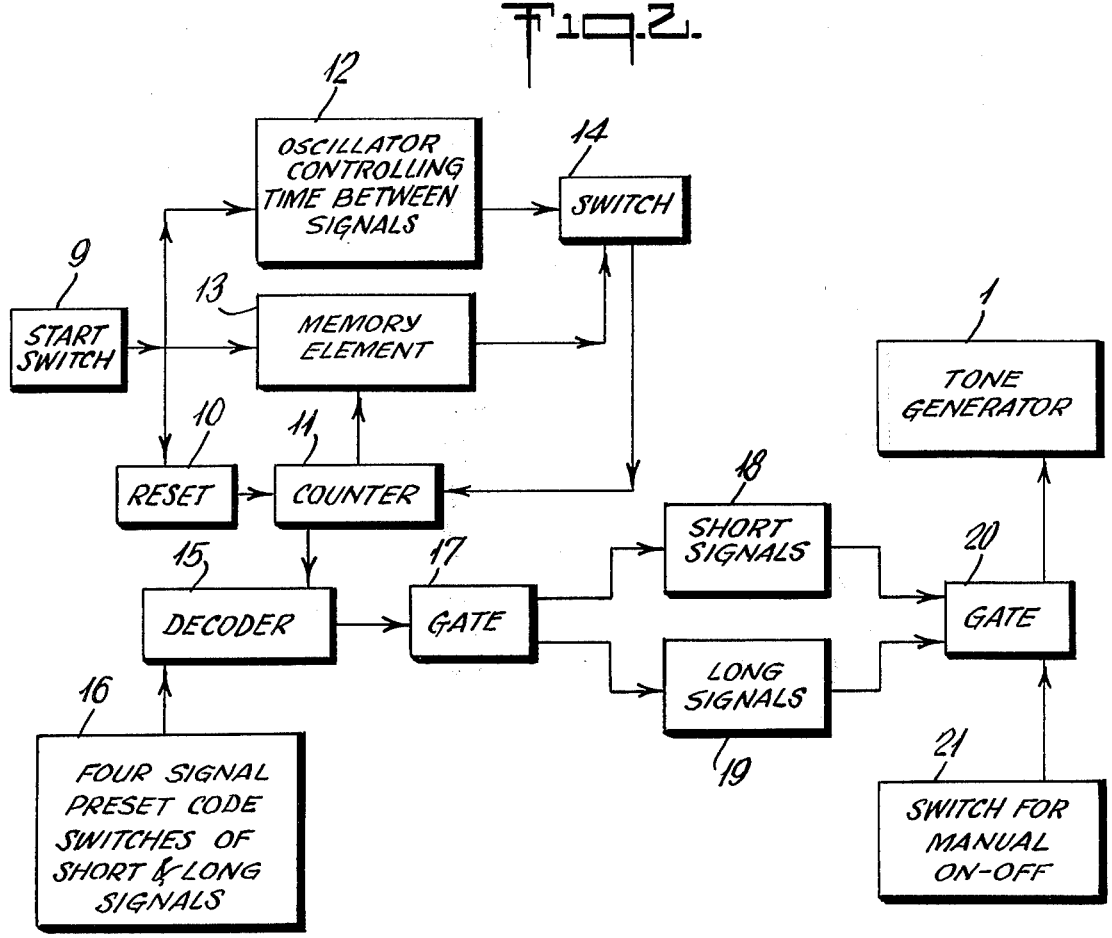
Figure 3:
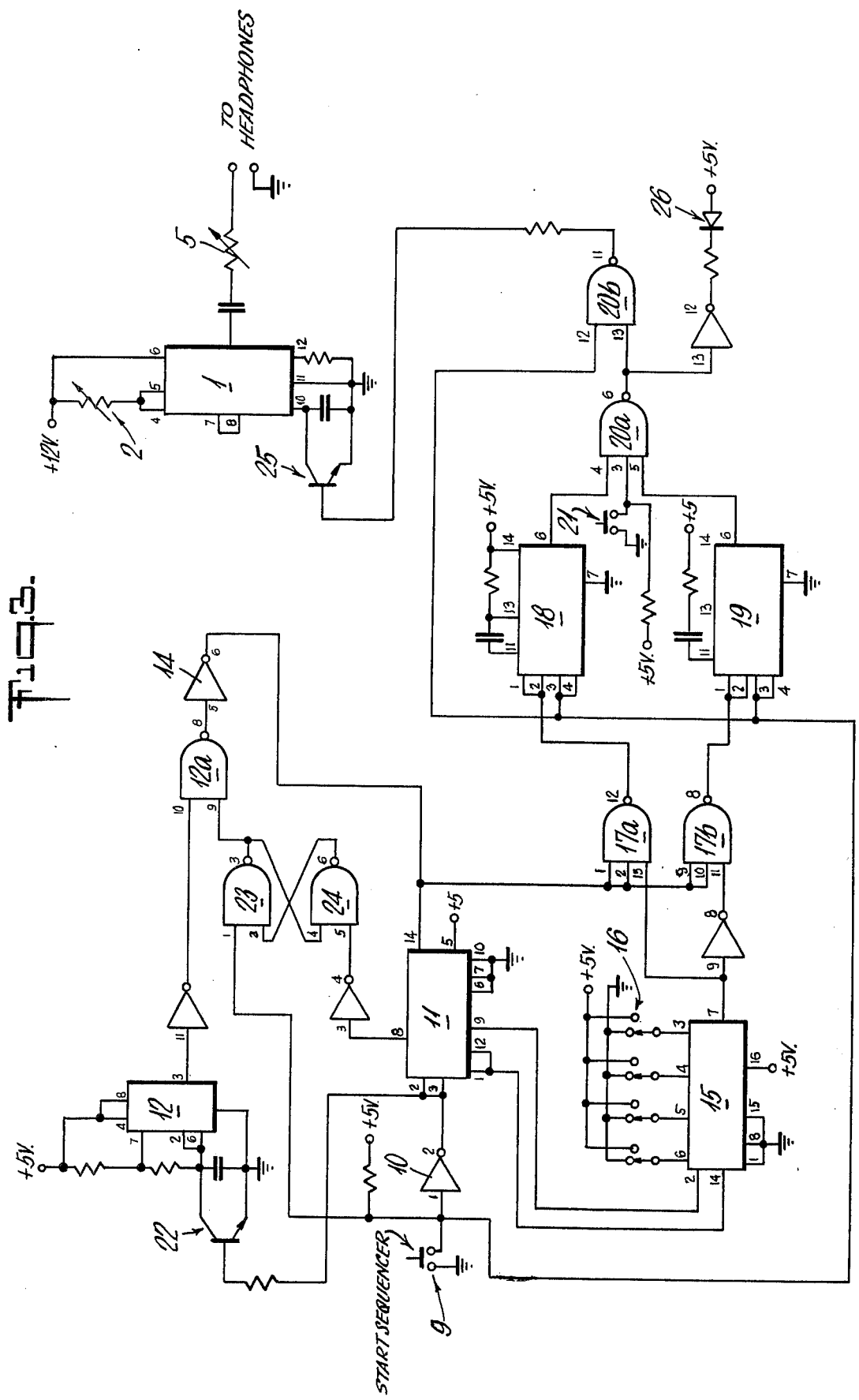

This invention achieves these purposes by a novel and useful combination of electronic circuits which can be better understood with reference to the drawings, in which FIG. 1 is a block diagram of the overall instrument, FIG. 2 is a block diagram of one illustration of a preferred embodiment of the on-off control which operates to provide, automatically on demand, a preset arrangement of short and long signals to the instrument, FIG. 3 is a schematic wiring diagram of the overall preferred embodiment including the preferred automatic preset signal control, and FIG. 4 is a stylized representation of the signals generated by the wiring of FIG. 2 as set forth in detail in FIG. 3.

In detail, the block diagram of FIG. 1 shows that ordinary alternating current (AC) is transformed to direct current (DC) which is fed to a tone generator 1 and to a frequency control 2, which can be either continuously adjusted or set to a group of precalibrated frequencies, usually and preferred a group of three frequencies. These frequencies can be calibrated in advance or the instrument can be integrated by standard electrical coupling, not shown, to the AC standard frequency available as the power source so as to give automatically fractions and/or multiples of that frequency. The tone generator 1 is connected through an on-off control 3 to ground 4 to complete the tone generation circuit. The on-off control can be any electrical switch. For manual control of the signals, a standard telegraph key is convenient. Alternatively, it can be any electronic means for automatically providing an on-off pre-set sequence, one embodiment of which is illustrated in the other Figures. The tones generated by 1 are fed through a volume control 5 to a switch 6 which is arranged to deliver said tones to one or the other or both of two earphones placed on the left 7 and right 8 ears of the subject being tested.

The block diagram of FIG. 2 shows a preferred embodiment which provides a system for automatically and electronically feeding to the tone generator a preset pattern of on-off signals. A start switch 9 causes a reset switch 10 to set a counter unit 11. An oscillator 12 is then started. Simultaneously a memory element 13 has activated a switch 14 which permits the oscillator 12 to feed to the counter 11 a rhythmic beat. The counter 11 then feeds to a decoder 15, via various connections, a composite unitary count of the beats. By a set of manual switches 16, the decoder feeds through a gate 17 into either a short signal generator 18 or a long signal generator 19 a series of impulses as directed by the pre-set switches 16 into one or the other of 18 or 19. These signal generators 18 and 19, in turn feed into a gate 20 either a long or a short, as the case may be, "on" signal. Gate 20 then feeds the integration of these signals, as timed previously by the oscillator 12, into the tone generator 1. Alternatively, a manual on-off switch 21, which can be a standard telegraph key or a plain on-off switch to provide continuous tone, also feeds through gate 20 to the generator 1.

In FIG. 3, a schematic wiring diagram of the embodiment of FIG. 2 is shown, with the various pins of the solid state units used for each function identified. The starter 9 causes the reset 10 to put the counter 11 in a start position. Simultaneously it feeds through a delay switch 22 a delayed initiation of the timing by oscillator 12 through NAND gate 12a. Also it feeds through a pair of cross connected NAND gates 23 and 24 which alternately control the feed through gate 14 by way of NAND gate 12a. When one set of signals have been fed through one of 23 or 24, the other causes a flip-flop to shut off the signal until a new one is initiated. The time-spaced signal emitted from switch 14 passes through the counter 11 which emits from different pins a set of timed low and high signals plus another signal feeding back into the memory element 13 at the end of four beats to shut off the sequence. The pre-set code switches 16 direct the signals at each beat into one or another NAND gate 17a or 17b and from them respectively into the short and long signal generators 18 and 19. These in turn feed the generated signals through NAND gates 20a and 20b to emit an integration of the pre-set signals, which in turn feeds into a switch 25. A low signal fed into switch 25 causes the tone generator 1 to turn on and a high signal shuts it off, thus generating the audible signal in the pre-set pattern. Alternatively, manual switch 21 can feed a signal through gates 20a and 20b to give a manually operated signal. A light 26 is suitably attached to give visual signal that a tone is being generated.

In FIG. 3, the frequency adjustment 2 and the volume adjustment 5 are shown as continuously variable but preferably they are preset ot precalibrated levels, usually three of each.

FIG. 4 shows diagrammatically how the signals are generated at each key place in the circuitry of FIG. 3. The start switch 9 put a short low signal on the system which initiates oscillator 12. Simultaneously, the memory element 13 emits a signal. The oscillator then emits a steady high signal with spaced low beats which is inverted by NAND gate 12a and emitted by switch 14 as a low signal with spaced high beats. Counter 11 puts out of pin 12 a set of alternately high and low steady signals, each reversal at a beat from switch 14. From pin 9, it puts out a set of alternately high and low signals changed at every other beat. From pin 11 it changes from low to high at the end of four beats and causes NAND gate 24 to flip-flop the signal and stop it until reinitiated. (The starter 9 can be continuously pushed to achieve a repeated sequenced signal or it can be an on-off switch which, in the on position, achieves this result by repeating the cycle.) The NAND gate 17 feeds the beats coded in the decoder 15 for short signals through one pin and gate 17a into the short signal generator 18 and through another pin and gate 17b those for long signals into the long low signal generator 19. The two then emit respectively short or long low signals at the indicated beats. These in turn are integrated through the NAND gates 20a and 20b into an integrated signal with short or low signals, as preset, at each beat.

In an alternative wiring the short and long signal generators 18 and 19 can be combined into one solid state unit, feeding from different pins. It will be apparent to those skilled in the art that other variant electronic means can be constructed to generate automatically a pre-set signal.

In the use of this invention, the subject assumes the earphones. Hearing in each ear or both together is tested at various frequencies and volumes using a continuous signal and the proper setting of the switches controlling the earphones, the frequency and the volume. Each ear is then tested at various frequencies and volumes using a preset signal. The subject must be able to recognize whether the signal is the same on each test at each volume and frequency on each ear. Failure to recognize changes shows lack of auditory memory. Better response in one ear than the other shows hearing side dominance.

This invention, as herein described, is a small, compact, portable instrument, unlike those used in the past for such purposes. Further, where in the past several instruments or machines had to be used, all these tests are combined in the one compact instrument.

I claim:

1. A compact portable apparatus for screening human subjects for deafness, auditory memory and hearing side-dominance which comprises, in combination
   a. electronic means for generating audible frequencies;
   b. means for converting said audible frequencies into sounds delivered separately to the individual ears of a human subject;
   c. means for controlling the delivery of said sounds into one or the other ear of said human subject or to both ears;
   d. means for controlling the delivery of said sounds (as continuous sounds or interrupted) in a preset pattern of long and short pulses
   e. means for control of the audible volume of said sounds; and
   f. means for control of the frequency of said sounds.

2. The apparatus of claim 1 in which the said means for controlling delivery of said sounds as continuous or intermittent signals is a manually operated electrical switch.

3. The apparatus of claim 1 in which the said means for controlling delivery of said sounds as continuous or intermittent signals is an electronic means for presetting delivery of a predetermined combination of long and short intermittent or alternatively of a continuous signal.

4. The apparatus of claim 3 in which said means for control of the audible volume is means for delivering three predetermined volumes.

5. The apparatus of claim 3 in which the said means for control of the frequency of said sounds is means for delivery of three predetermined frequencies.

6. The apparatus of claim 4 in which said means for control of the frequency of said sounds is means for delivery of three predetermined frequencies.

* * * * *